(12) United States Patent
Arnold et al.

(10) Patent No.: US 11,744,774 B2
(45) Date of Patent: Sep. 5, 2023

(54) ADJUSTABLE BOTTLE SUPPORT

(71) Applicant: Keymed (Medical & Industrial Equipment) Limited, Southend-on-Sea (GB)

(72) Inventors: Adam Arnold, Southend-on-Sea (GB); Jordan Jowitt, Southend-on-Sea (GB); Timothy Roberts, Southend-on-Sea (GB); Nicholas MacMillan, Southend-on-Sea (GB); Nevzat Atakan, Southend-on-Sea (GB)

(73) Assignee: Keymed (Medical & Industrial Equipment) Limited, Southend-on-Sea (GB)

( * ) Notice: Subject to any disclaimer, the term of this patent is extended or adjusted under 35 U.S.C. 154(b) by 29 days.

(21) Appl. No.: 17/535,265

(22) Filed: Nov. 24, 2021

(65) Prior Publication Data
US 2022/0125679 A1 Apr. 28, 2022

Related U.S. Application Data

(63) Continuation-in-part of application No. 17/503,640, filed on Oct. 18, 2021.

(30) Foreign Application Priority Data

Oct. 22, 2020 (GB) ..................... 2016779
Sep. 6, 2021 (CN) .................. 202111037935.3

(51) Int. Cl.
*B65D 23/00* (2006.01)
*A61J 1/16* (2023.01)
*F16M 11/20* (2006.01)

(52) U.S. Cl.
CPC ............ *A61J 1/16* (2013.01); *F16M 11/2021* (2013.01); *A61J 2200/42* (2013.01); *B65D 23/001* (2013.01)

(58) Field of Classification Search
USPC ....... 248/130, 133, 134, 135, 136, 137, 138, 248/139, 140, 141, 142, 144, 149, 349.1,
(Continued)

(56) References Cited

U.S. PATENT DOCUMENTS 5,488,882 A * 2/1996 Riemersma ............ B65G 65/23
414/419
6,655,563 B2 * 12/2003 Shimajiri ............... B60N 3/102
248/311.2

(Continued)

FOREIGN PATENT DOCUMENTS

CN 202061091 U 12/2011
CN 203075219 U 7/2013
(Continued)

OTHER PUBLICATIONS

United Kingdom Intellectual Property Office, Search Report in United Kingdom Patent Application No. GB2016779.7, 1 p. (dated Mar. 16, 2021).

(Continued)

*Primary Examiner* — Alfred J Wujciak
(74) *Attorney, Agent, or Firm* — Leydig, Voit & Mayer, Ltd.

(57) ABSTRACT

An adjustable bottle support for a pump used in medical procedures comprises first and second support members mounted on an attachment member which is attachable to a pump body. The second support member is pivotally mounted on the attachment member for rotation between a first position in which in which the first and second support members are aligned and level with one another and a second position in which the second support member is tilted and slopes upwardly in a direction away from the first support member.

20 Claims, 16 Drawing Sheets

(58) Field of Classification Search
USPC ..... 248/346.06, 346.03, 905, 458, 455, 454,
248/447, 457, 310, 311.2, 102, 103, 104,
248/105, 106, 314, 316.8; 222/173, 609,
222/180, 181.3, 103, 184
See application file for complete search history.

(56) References Cited

U.S. PATENT DOCUMENTS

| | | | |
|---|---|---|---|
| 7,748,417 B2 * | 7/2010 | Arcuri | B67D 1/127 |
| | | | 141/192 |
| 8,118,318 B1 * | 2/2012 | Chauza | B62B 1/16 |
| | | | 280/47.3 |
| 2005/0035167 A1 | 2/2005 | Threet et al. | |
| 2006/0124807 A1 * | 6/2006 | Nice | B67D 7/845 |
| | | | 248/140 |
| 2013/0112831 A1 * | 5/2013 | Kong | B60N 2/793 |
| | | | 248/311.2 |
| 2014/0330205 A1 | 11/2014 | Tian | |
| 2018/0228697 A1 | 8/2018 | Dedvukaj et al. | |
| 2018/0252467 A1 * | 9/2018 | Neal | A47G 23/0216 |

FOREIGN PATENT DOCUMENTS

| | | |
|---|---|---|
| CN | 203408257 U | 1/2014 |
| CN | 111135389 A | 5/2020 |
| WO | WO 96/24396 A1 | 8/1996 |

OTHER PUBLICATIONS

European Patent Office, Extended European Search Report in European Patent Application No. 21200715.7, 6 pp. (dated Mar. 18, 2022).

\* cited by examiner

ADJUSTABLE BOTTLE SUPPORT

CROSS-REFERENCE TO RELATED APPLICATIONS

This application is a continuation-in-part of U.S. patent application Ser. No. 17/503,640, filed Oct. 18, 2021, and claims priority to Great Britain Patent Application No. GB 2016779.7, filed Oct. 22, 2020, both of which are incorporated by reference herein in their entireties for all purposes.

BACKGROUND

The present invention relates to an adjustable support or holder for medical equipment. In particular, the support is intended to support a bottle on a peristaltic pump, which is used to supply liquid from the bottle for a medical procedure such as an endoscopy.

Peristaltic pumps for medical procedures are frequently mounted on a shelf of a moveable workstation or trolley which also carries other equipment. Therefore, space is relatively limited. Typically, liquid is provided in a standard 1 litre disposable bottle which may be cylindrical or square in cross-section and is mounted on a support fixed to the side of the pump. However, for some procedures bottles of larger capacity are desired but cannot fit on a support intended for the standard bottles. There is a need to support various different sizes and configurations of bottle adjacent to the pump within the limited space available, ensuring the bottle is secure but easily accessible so that it can be replaced when empty.

SUMMARY

The present invention provides an adjustable bottle support for a pump, comprising a first support member and a second support member for supporting parts of a bottle, the first and second support members mounted on an attachment member which is attachable to a pump body, wherein the second support member is pivotally mounted on the attachment member for rotation between a first position in which in which the first and second support members are aligned and level with one another and a second position in which the second support member is tilted and slopes upwardly in a direction away from the first support member. The bottle support of the invention is therefore easily adjustable in order to accommodate different shapes and sizes of bottle.

Preferably, the first and second support members each comprise a base with front, rear and side edges, wherein in the first position, the front edge of the first support member and the rear edge of the second support member are level with each other, the second support member is rotatable about a pivot axis between its front and rear edges, and in the second position the rear edge of the second support member is lower than the front edge of the first support member.

The first support member may further comprise a downward sloping wall depending from the front edge. In this case, in the second position, the angle between the base of the second support member and the downward sloping wall of the first support member is preferably approximately 90 degrees. These features allow a smaller bottle to be located securely on the holder.

In one embodiment, the first support member is integral with the attachment member. In another embodiment, the first support member is releasably mountable on the attachment member in first and second positions. In this case, preferably in the first position the first support member is horizontal and in the second position the first support member is tilted and slopes upwardly in a direction away from the second support member.

The first support member may further comprise a base with a front edge which is closest to the second support member, a rear edge which is furthest from the second support member and a retaining wall which is movably attached to the first support member for movement between a retracted position close to the rear edge and an extended position further from the rear edge. The wall helps to position and retain a bottle on the holder and is movable to accommodate different bottle sizes.

The second support member may be pivotally mounted on the attachment member by a pivot axle and further comprise a detent on the second support member selectively engageable with the attachment member to retain the second support member in the first and second positions.

Alternatively, the second support member may be pivotally mounted on the attachment member by a pivot mechanism which comprises three pivot pins extending from the attachment member and arranged in a triangular configuration, the pivot axis of the second support member passes through the centre of the triangular configuration, and the second support member comprises a side wall with three arcuate slots centred on the pivot axis, wherein each pivot pin extends through one of the slots. Preferably, each slot comprises first and second ends and a notch is formed at each end for receiving a pivot pin in the first and second positions respectively. The notches may be positioned such that in the first and second positions the weight of the second support member acts to retain each pin in a notch.

Where a detent is provided it may comprise a resilient arm on the second support member with a projection selectively engageable with first and second openings in the attachment arm. The resilient arm may further comprises a grip portion protruding from the arm and operable by a user to selectively engage and disengage the projection with the first and second openings in the attachment arm.

Optionally, the second support member may further comprise a heating device operable to heat fluid in a bottle supported thereon and/or an illumination device operable to illuminate a bottle supported thereon.

The adjustable bottle support may further comprise a flap attached to the second support member and moveable to a deployed position to hold the second support member in the second position. Also, the first support member may further comprises a downwardly extending support leg. Such features help to support the weight of a bottle mounted on the device.

DESCRIPTION OF DRAWINGS

The invention will now be described in detail, by way of example only, with reference to the accompanying drawings in which.

DETAILED DESCRIPTION

The adjustable equipment holder of the present invention generally comprises a first support tray, a second support tray and an attachment member 16. The attachment member is used for attaching the holder to a pump body. One or both support trays are moveable relative to the attachment member in order to support items of different sizes.

Figure 1:
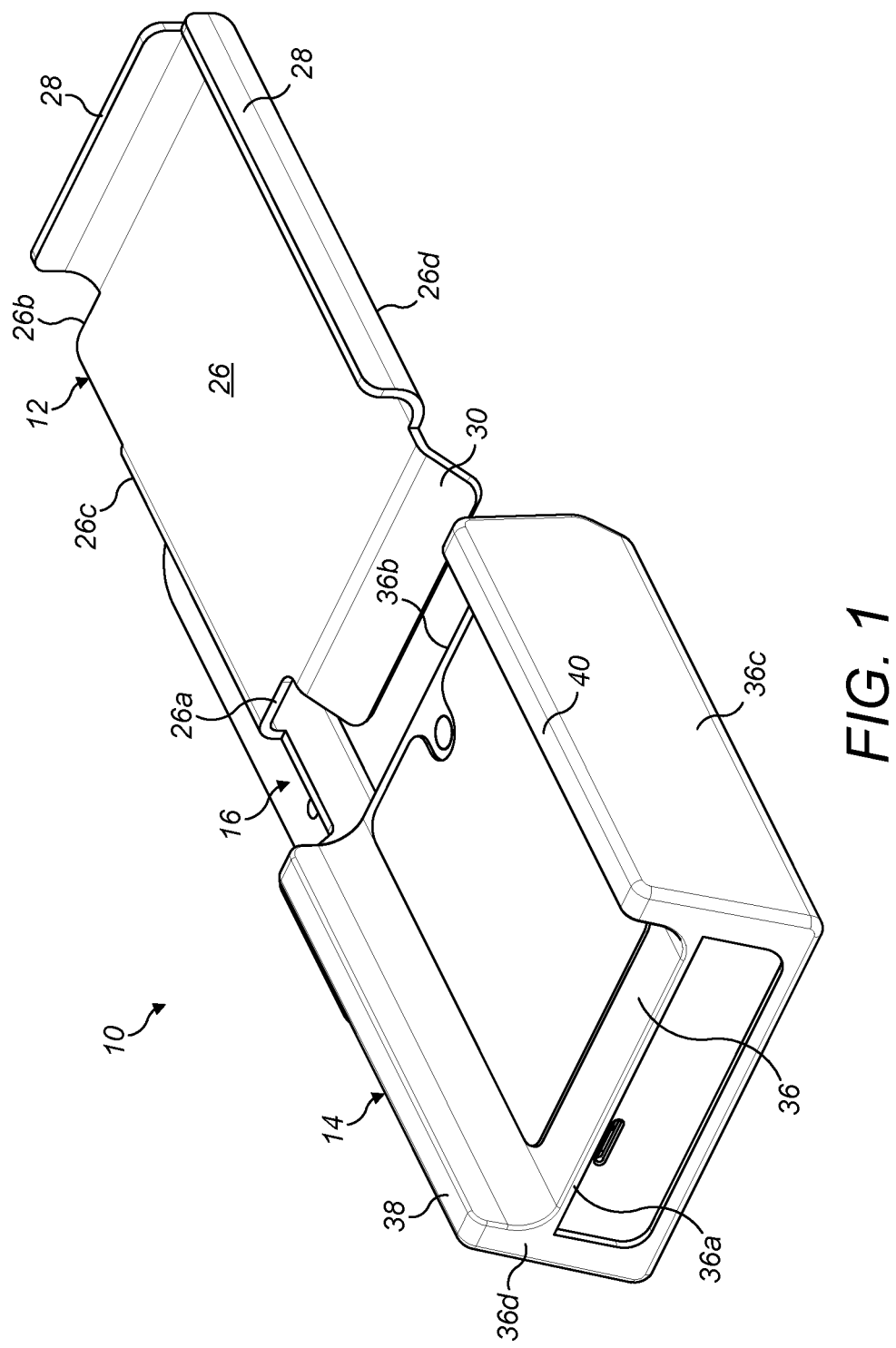
FIG. 1 shows an adjustable support in accordance with one embodiment of the present invention in a first, flat orientation.
Figure 2:
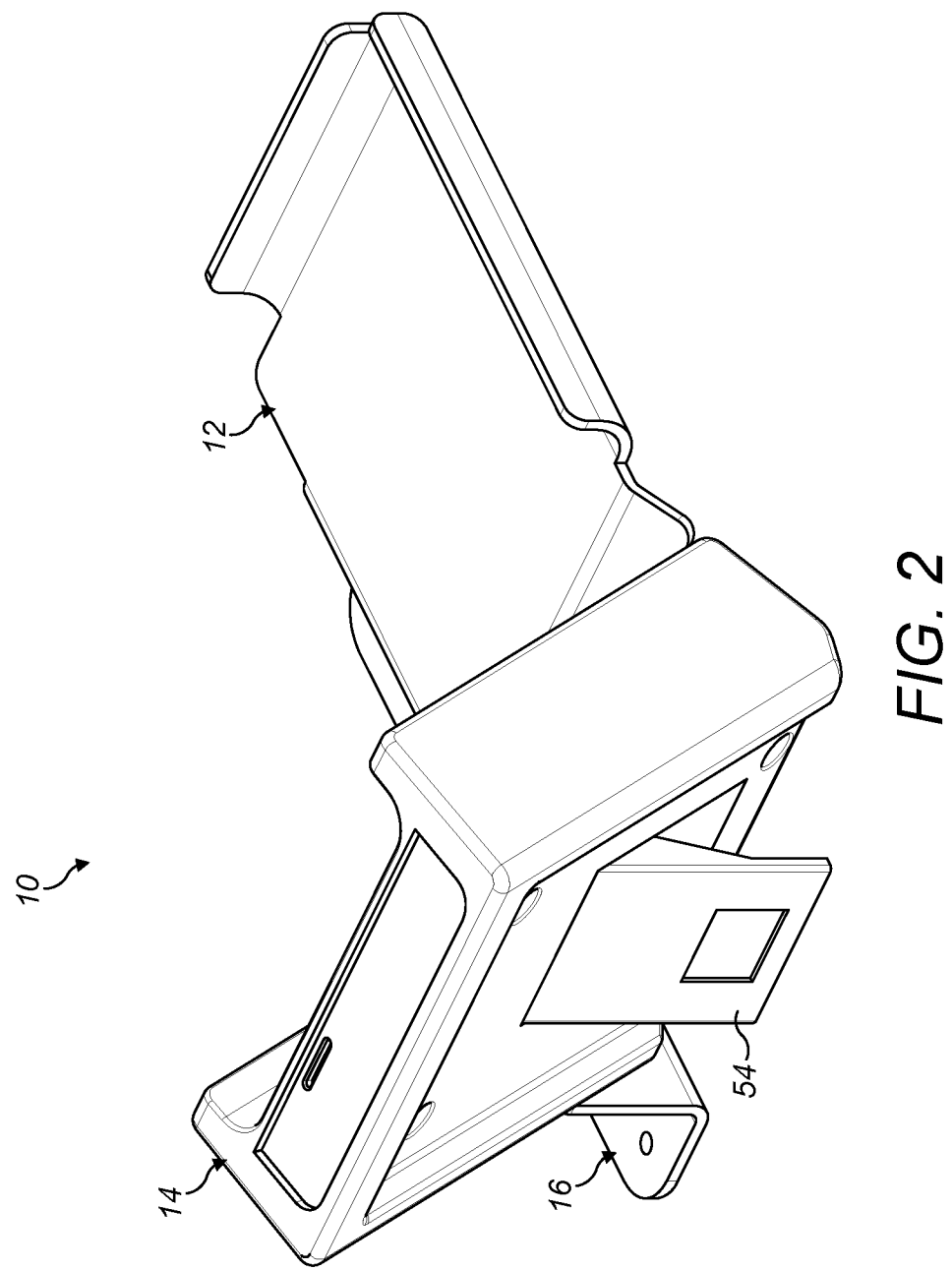
FIG. 2 shows the support of FIG. 1 in a second, folded configuration.

An adjustable equipment holder 10 in accordance with a first embodiment of the present invention comprises a first, fixed support tray 12, a second, moveable support tray 14 and an attachment arm 16. The attachment arm 16 is used for attaching the holder 10 to a pump body 18 (which is shown schematically in FIGS. 3 and 4) and as an attachment point for a pivot mechanism 20 which allows the second tray 14 to move between first and second positions. In the first position, the moveable tray 14 is flat and level with the fixed tray 12 as shown in FIG. 1. In the second position, the moveable tray 14 is tilted, for example at an angle of about 50 degrees to the horizontal, and slopes upwardly in a direction away from the fixed tray 12 as shown in FIG. 2. In this position, the rear edge of the moveable tray 14 is lower than the front edge of the fixed tray 12.

Figure 3:
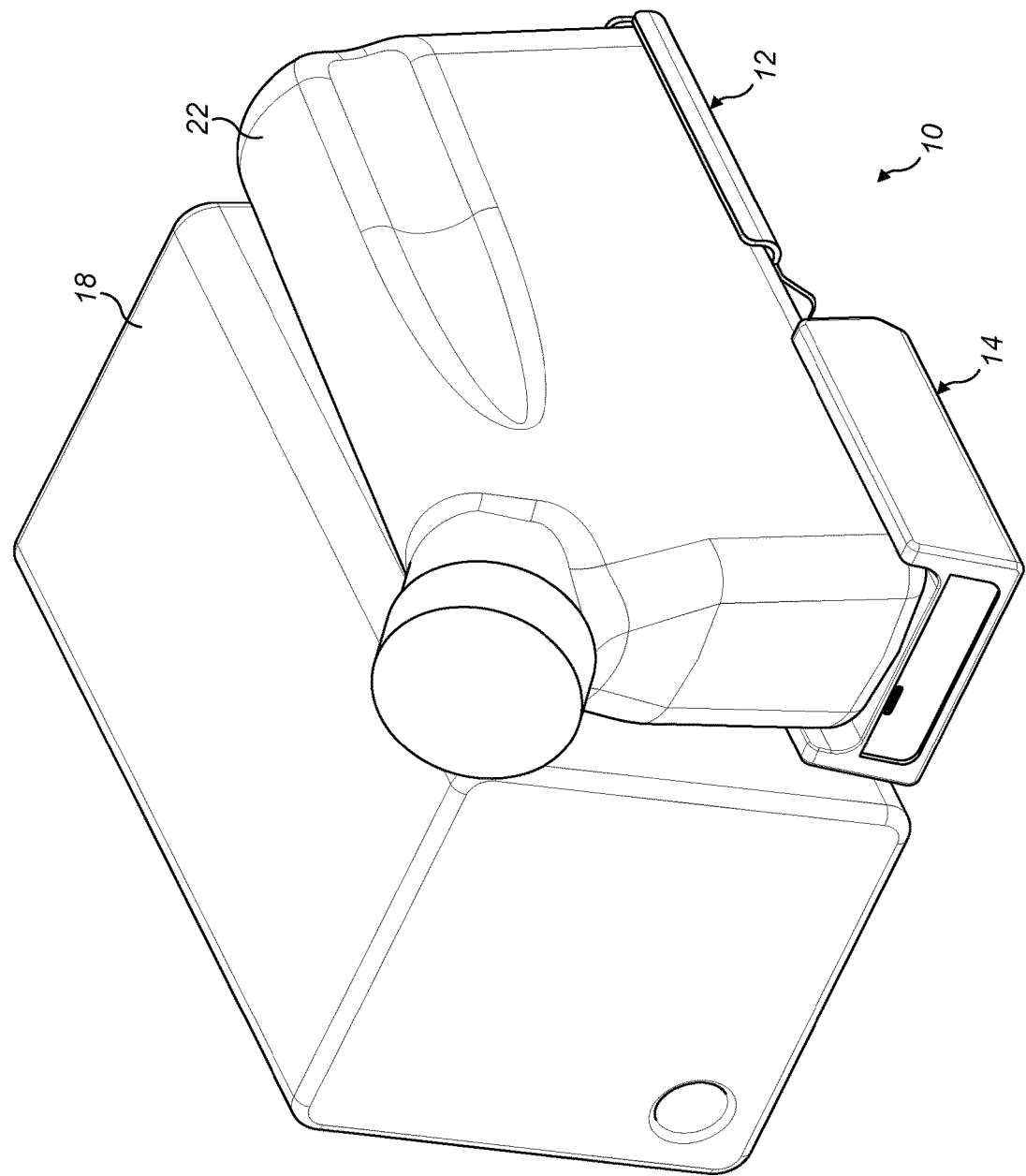
FIG. 3 shows a pump body and the adjustable support of FIG. 1 in the first, flat orientation with a bottle supported thereon.

As shown in FIG. 3, when the holder 10 is in the first, flat position, a larger bottle 22, or other item of equipment, can be supported across the surface of both the first, fixed tray 12 and second, moveable tray 14.

Figure 4:
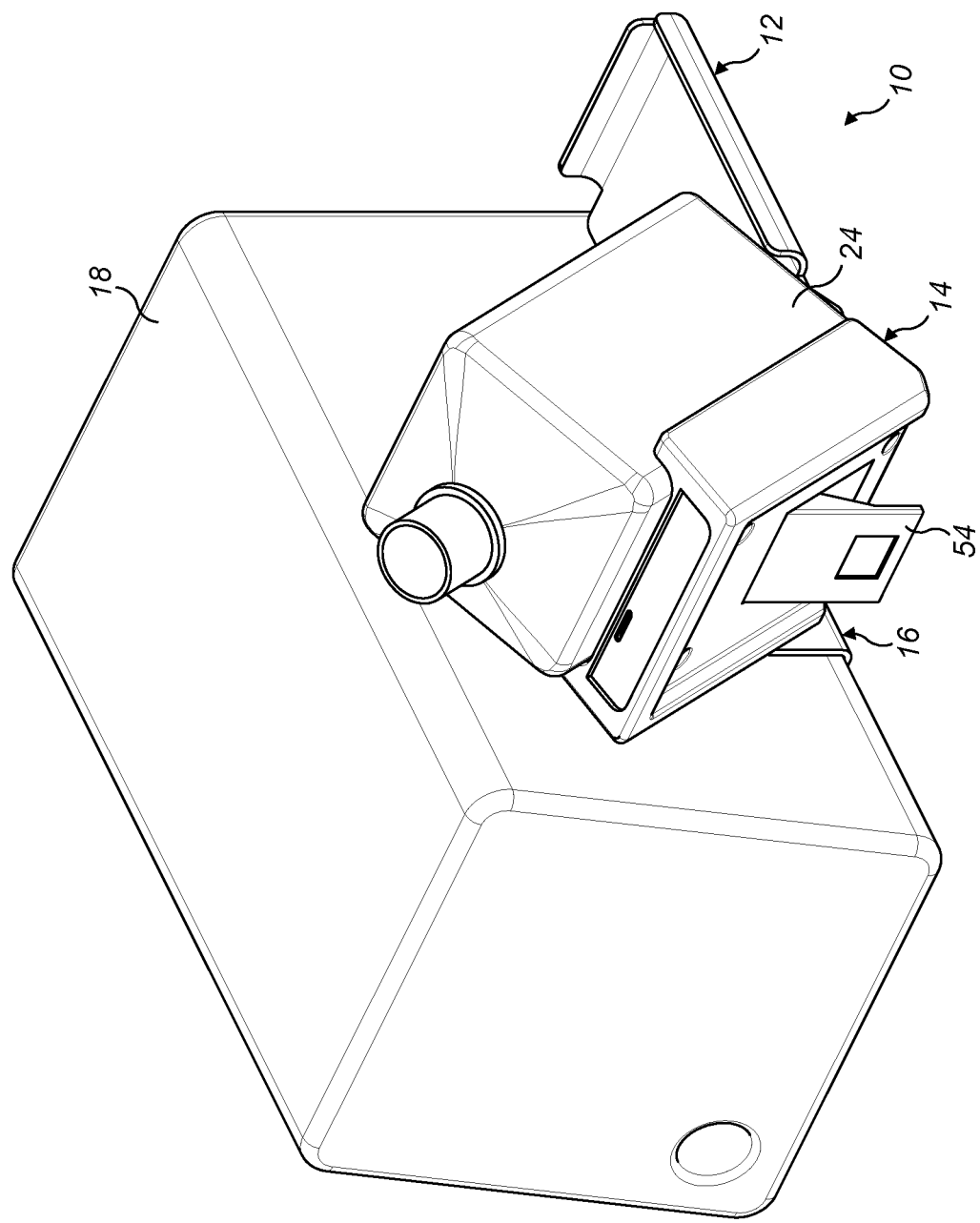
FIG. 4 shows a pump body and the adjustable support of FIG. 2 in the second, folded orientation supporting a different form of bottle.

As shown in FIG. 4, in the second, tilted position a smaller bottle 24, or other item of equipment, can be supported. The side of the bottle 24 rests against the surface of the moveable tray 14. The base of the bottle 24 rests against the front edge of the fixed tray 12.

The first, fixed tray 12 comprises a flat base 26 with front, rear and opposing side edges 26a-d. The rear edge 26b, and the side edge 26c which will be furthest from the pump body 18 in use, are preferably formed with upturned walls 28. The front edge 26a is formed with a downward sloping wall 30. Preferably, this slopes at approximately 40 degrees to the horizontal.

Figure 5:
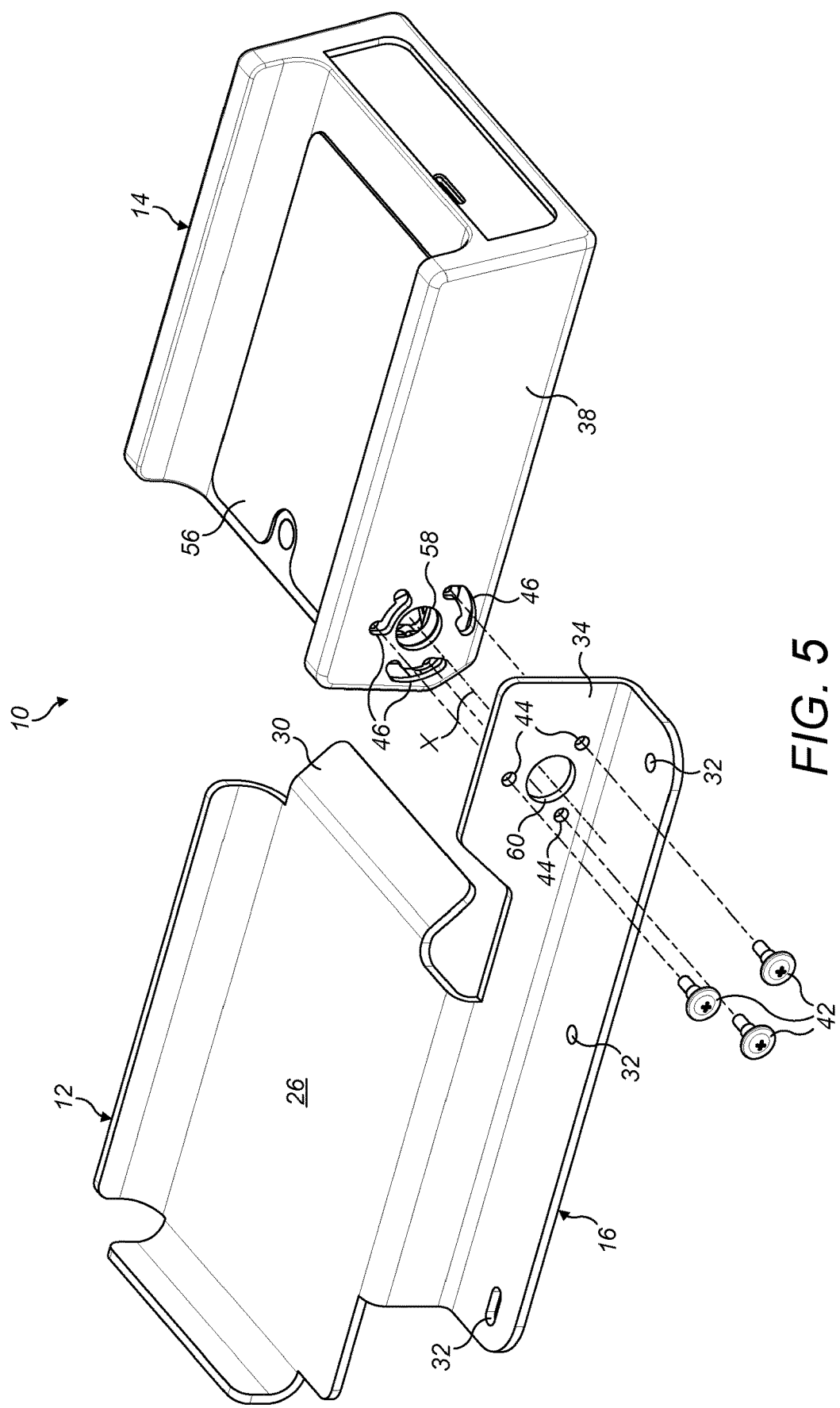
FIG. 5 is an exploded view of an adjustable support with one embodiment of pivot mechanism.

In this example, the attachment arm 16 for attaching the holder 10 to a pump body 18 extends from the other side edge 26d. This is best seen in FIG. 5. The fixed tray 12 and attachment arm 16 may be formed integrally, for example pressed from sheet metal or as a one-piece plastic moulding. Alternatively, they may be formed separately and bonded or mechanically joined together. The attachment arm 16 is shaped to locate against part of the pump body 18 and includes fixing holes 32 for attachment devices such as screws.

The attachment arm 16 includes a forward extension 34, protruding beyond the front edge 26a and sloping wall 30 of the fixed tray 12. This provides an attachment point for the moveable tray 14 and pivot mechanism 20.

The moveable tray 14 also comprises a flat base 36 with front, rear and opposing side edges 36a-d. First and second side walls 38, 40 are provided on the side edges 36c, d. These extend above and below the base 36. In use, the moveable tray 14 is mounted with the first side wall 38 adjacent to the forward extension 34 of the attachment arm 16 and pivots relative thereto. The moveable tray 14 optionally includes a heating device which is described further below. The moveable tray 14 may be formed as plastic moulding, particularly when a heating device is to be included. However, it may be formed from other materials, for example pressed from sheet metal.

The pivot mechanism 20 allows the moveable support 14 to pivot between the flat and angled positions and retains the moveable tray in each position without the need for additional components or tools.

In a first embodiment seen in FIG. 5, the pivot mechanism 20 comprises three pivot pins 42 arranged in a triangular configuration. The pins 42 pass though openings 44 in the attachment arm 16 and through arcuate slots 46, 48, 50 in the first side wall 38 of the movable tray 14 and are fixed to a plate 52 mounted beneath the base 36 of the moveable tray 14. The attachment arm 16, pins 42 and the plate 52 all remain stationary and the tray 14 is able to rotate relative to them by sliding the arcuate slots 46, 48, 50 over the pins 42. The pivot axis X passes through the centre of the triangle defined by the pins 42.

As best seen in FIGS. 6A-D, each slot 46 comprises an arcuate portion which forms part of a circle centred on the pivot axis X. Each slot 46 also has a notch 48, 50 at each end. The uppermost slot has notches 48, 50 extending outwardly away from the pivot axis X. The two lower slots have notches 48, 50 extending inwardly towards the pivot axis X. FIGS. 6A to 6D illustrate how the pins 42 move relative to the slots 46 as the moveable tray 14 is pivoted between the flat and angled orientations.

Figure 6A:
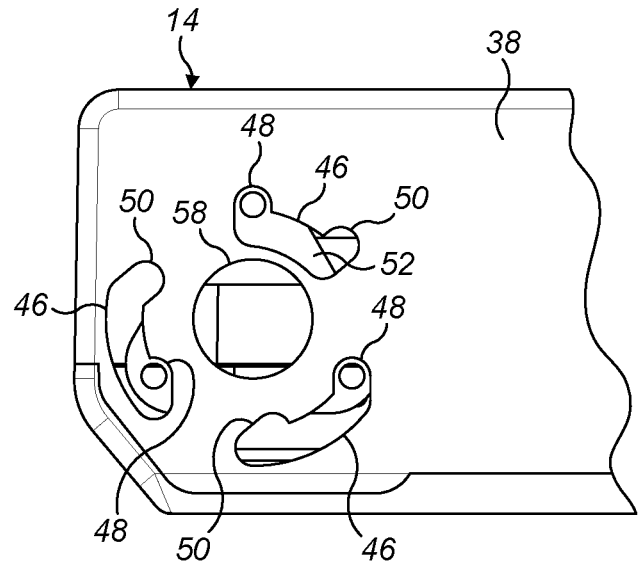
FIGS. 6A to 6D are detailed views of the pivot mechanism of the support of FIG. 5.
Figure 6B:
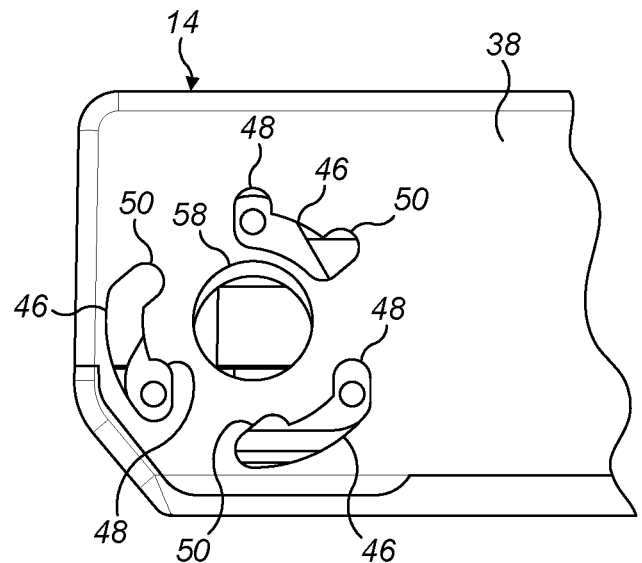
Figure 6C:
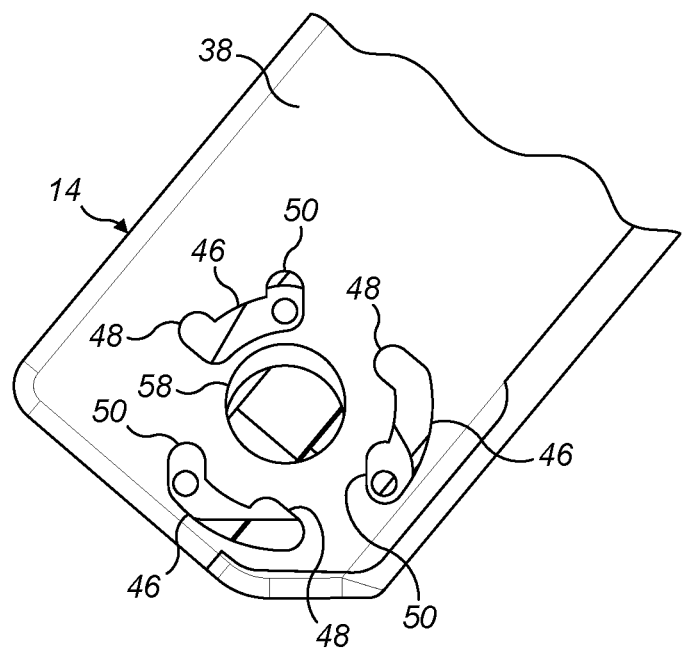
Figure 6D:
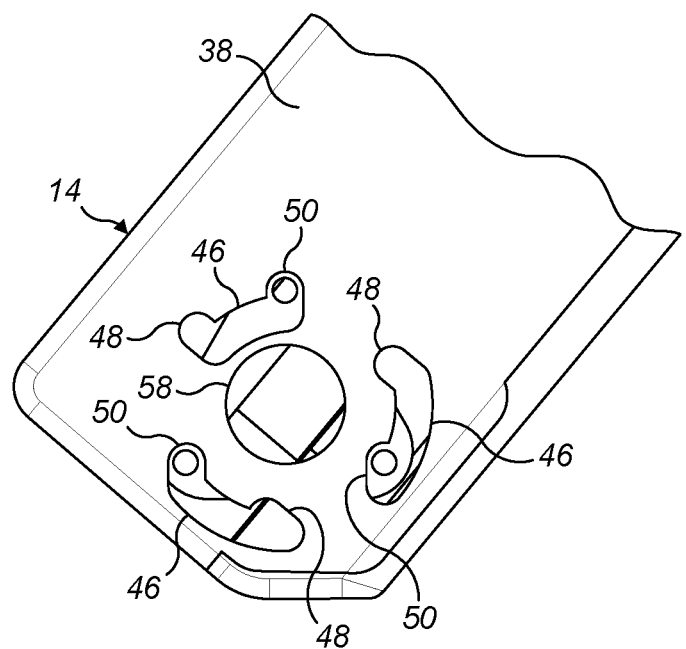

In a first position shown in FIG. 6A, each pivot pin 42 is located in a notch 48 at a first end of its respective slot 46 and the moveable tray 14 is locked in the flat position. In order to change the orientation of the tray 14, the tray 14 is first raised in order to move each pin 42 out of the notch 48 into the arcuate portion of its slot 46, as seen in FIG. 6B. The tray 14 can then be rotated (anticlockwise in the figures) such that each pin 42 moves along the arcuate portion of the slot 46 to the other end, as shown in FIG. 6C. The moveable tray 14 is then lowered in order to engage each pin 42 in the notch 50 at that second end of the slot 46, as shown in FIG. 6D.

Thus, in both the flat and tilted positions, the weight of the tray 14 itself (and any bottle supported on it) pushing the tray 14 downwards acts to retain the pins 42 in the notches 48, 50. To move the tray 14 it is only necessary to slightly raise it in order to move each pin 42 out of the relevant notch and into the arcuate portion of the slot 46.

The pivot axis X is located forward of the rear edge 36b of the moveable tray 14. Therefore, in the tilted position, the rear edge 36b of the moveable tray 14 is lower than the front edge 26a and base 26 of the fixed tray 12. When a smaller bottle 24 is positioned on the holder 10 as in FIG. 4, the side of the bottle 24 rests against the base 36 of the moveable tray 14 and the base of the bottle 24 rests against the sloping wall 30 at front edge of the fixed tray 12. The angle between the tilted moveable tray 14 and the sloping wall 30 is preferably approximately 90 degrees, to fit against the side and the bottom of the bottle 24. This locates the bottle 24 more securely than if the rear edge 36b of the moveable tray 14 remained at the same level as the base 26 of the fixed tray 12. Supporting the bottle 24 in the tilted position also makes it easier to ensure it can be fully emptied.

As mentioned above, the moveable tray 14 optionally includes a heating device 56 to warm fluid in a bottle resting thereon. Warming the fluid is desirable in many medical procedures. The heating device 56 may comprise an electrically heated plate set into the base 36 of the moveable tray 14. Wires or cables connecting the heating device 56 to a power supply may be routed out of the moveable tray 14 through an aperture 58 in the side wall 38 and a corresponding aperture 60 in the bracket 16. These apertures 58, 60 are located in the centre of the triangular configuration of the pivot pins 42 and arcuate slots 46, and are therefore centred on the pivot axis X and do not obstruct the pivoting movement of moveable tray 14. The moveable tray 14 optionally also includes an illumination device to illuminate a bottle mounted on the holder 10. As the bottles may be translucent or transparent, this helps to show the amount of fluid in the bottle so that it is easy to tell when the bottle is nearly empty and replacement is required.

In another embodiment, the overall structure of the holder 10 is the same as that described above, except for the pivot mechanism 20. In this case, the pivot mechanism 20 comprises a pivot pin connecting the moveable tray 14 to the attachment arm 16 and a resiliently biased or sprung detent on the moveable tray 14, selectively engageable with the attachment arm 16 at first and second locations, to retain the moveable tray 14 in the flat and tilted positions.

Figure 7A:
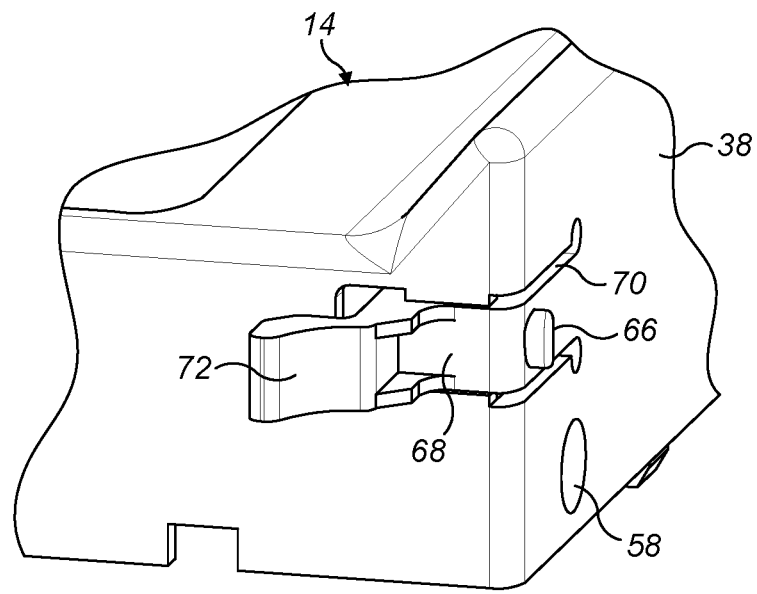
FIGS. 7A and 7B are detailed views of part of a second embodiment of the pivot mechanism.
Figure 7B:
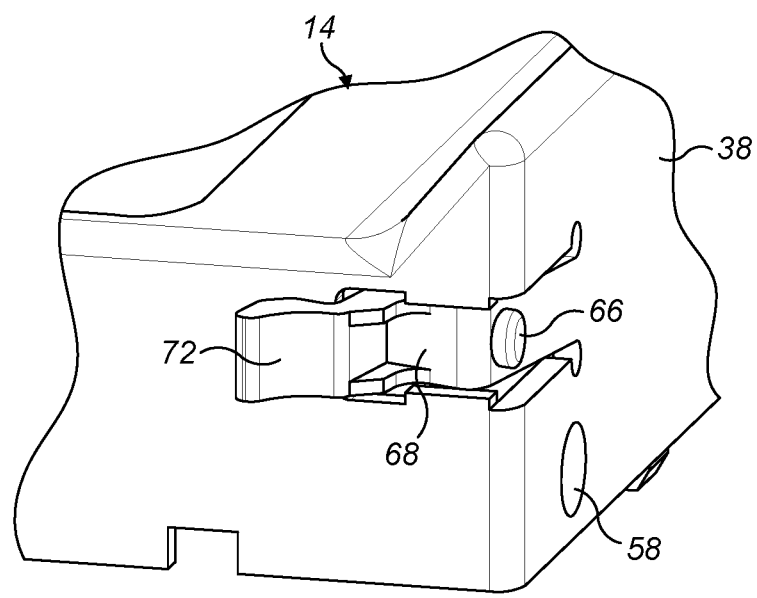
Figure 8:
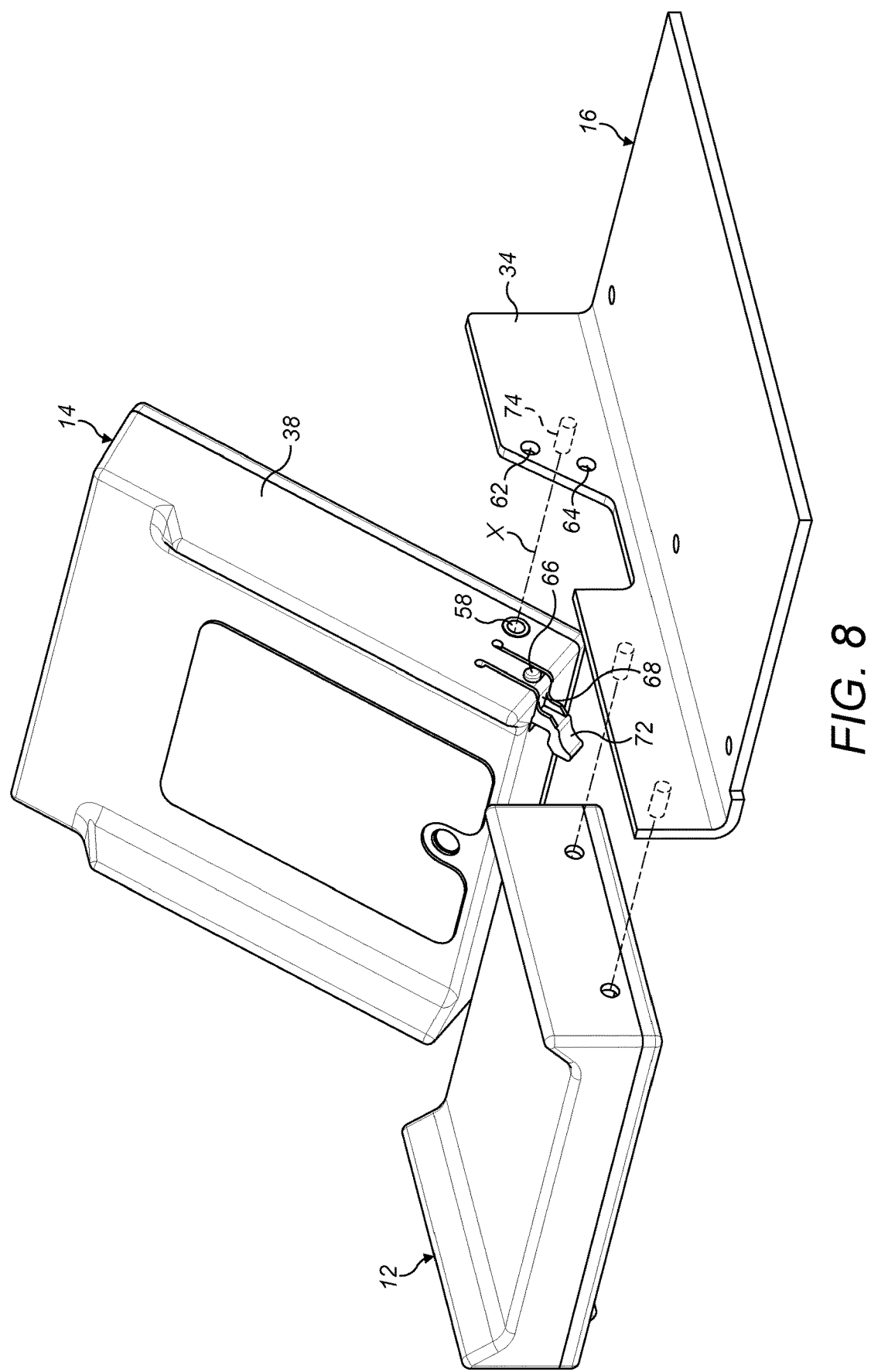
FIG. 8 is an exploded view of an adjustable support with the pivot mechanism of FIGS. 7A-B.

In the example shown in FIGS. 7A-B and 8, the attachment arm 16 is separate from the fixed tray 12 and can be attached to it with mechanical fasteners. The forward extension 34 is formed with upper and lower holes 62, 64 and the moveable tray 14 is formed with a projecting button 66 on a resilient lever arm 68. The lever arm 68 is integrally formed with the moveable tray 14 and defined by a slot 70 running around three edges of the arm 68. An extension on the end of the lever arm provides a grip 72 for the user. The moveable tray 14 is rotatably mounted on the attachment arm 16 by a pivot pin 74 secured to the attachment arm 16 which passes through the aperture 58 in the side wall 38 of the moveable tray 14.

When the moveable tray 14 is in the flat position, the projecting button 66 engages in the lower hole 64 to retain the tray 14 in that position. If a user pulls on the grip 72 the lever arm 68 flexes away from the attachment arm 16 and the button 66 releases from the hole 64, allowing the moveable tray 14 to rotate to the tilted position. Releasing the grip 72 allows the lever arm 68 to relax back towards the attachment arm 16 and engages the button 66 in the upper hole 62. The process is of course reversed to move the tray 14 back to the flat position.

To help support the weight of a bottle 24 when the holder 10 is in the tilted position, the moveable tray 14 may also include a flap or strut 54 which can fold out from its lower surface, as also shown in FIGS. 2 and 4. Such a flap 54 may be incorporated into a holder 10 with either form of pivot mechanism 20 described above. Alternatively, the moveable tray 14 may freely rotate on a pivot pin, without any additional form of catch or detent, and instead the flap 54 is simply deployed when the moveable tray 14 is tilted, or folded back against the lower surface of the moveable tray 14 when the latter is in the flat position.

Another embodiment of equipment holder 80 in accordance with the invention is shown in FIGS. 9-15. This equipment holder 80 comprises a first support tray 82 and a second support tray 84 both mountable on an attachment member in the form of a bracket 86. The bracket 86 is attachable to a piece of equipment such as a peristaltic pump 18, in a similar manner to attachment arm 16 shown in FIGS. 3 and 4 above.

In this embodiment both the first and second support trays 82 and 84 can be positioned in different locations on the bracket 86 in order to accommodate different sizes and shapes of bottle or other equipment.

Figure 9:
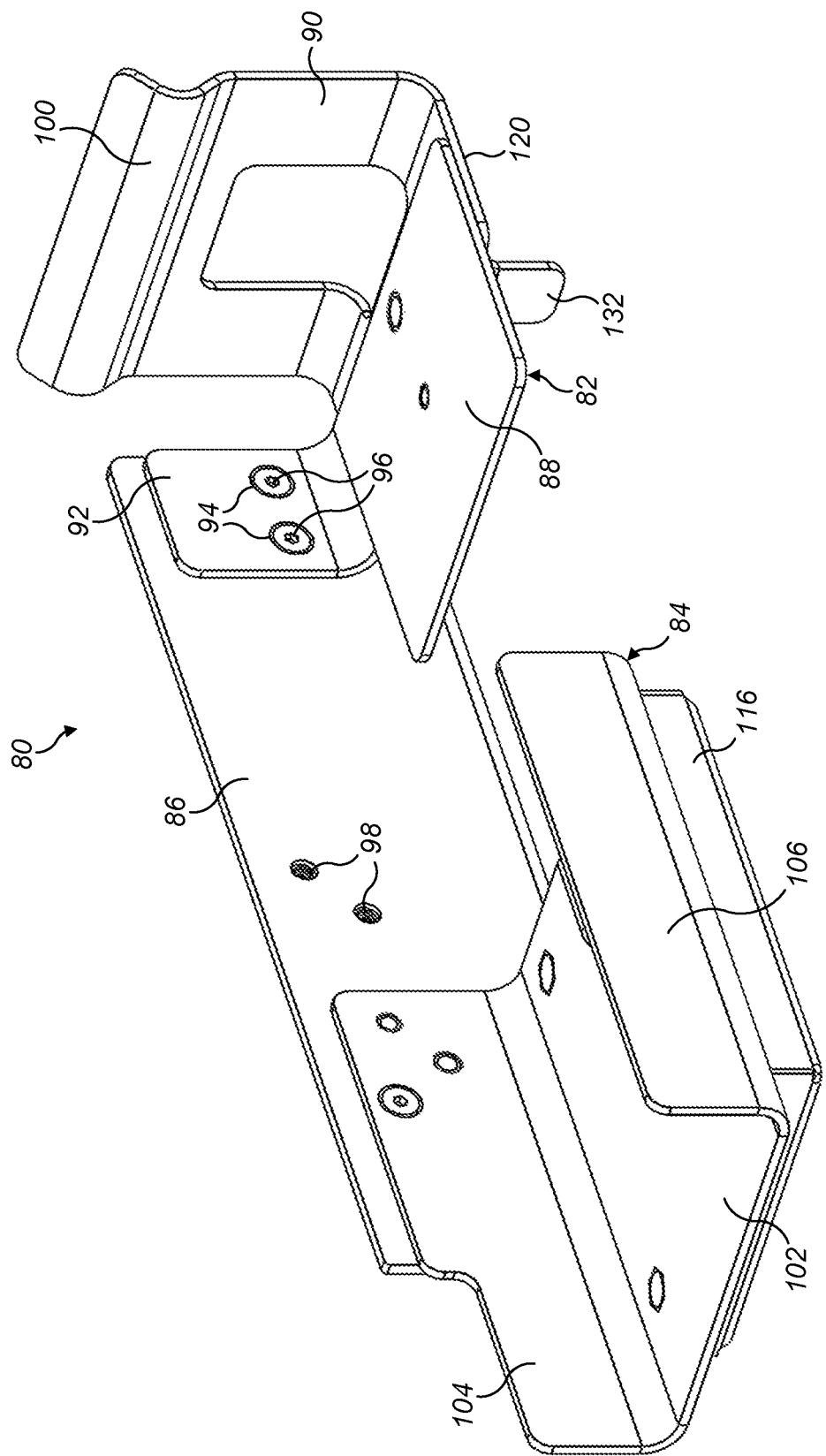
FIG. 9 is a perspective view from one side of an adjustable support in accordance with a second embodiment of the present invention, in a first, flat orientation.
Figure 10:
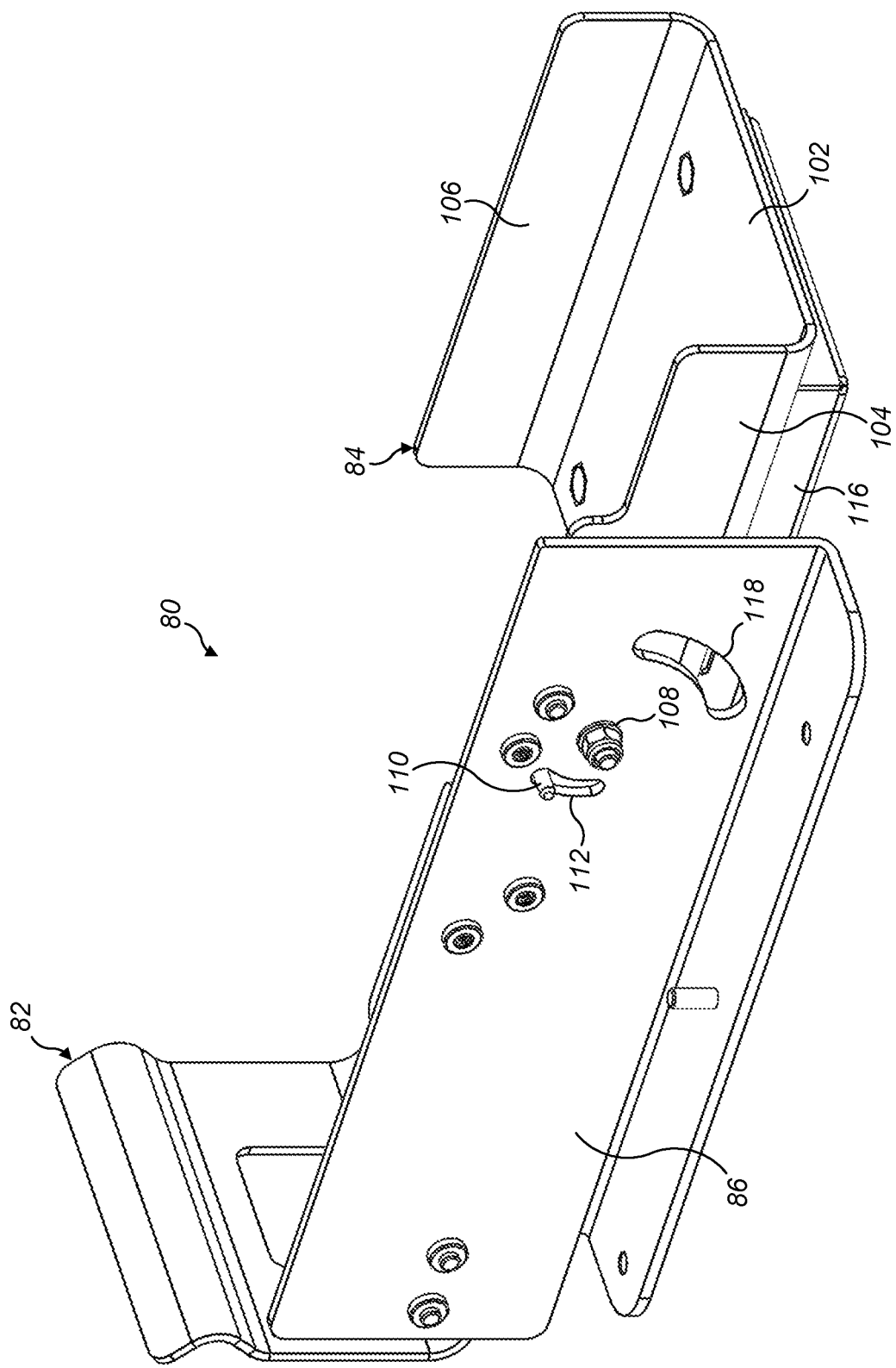
FIG. 10 is a perspective view from the other side of the adjustable support of FIG. 9.
Figure 11:
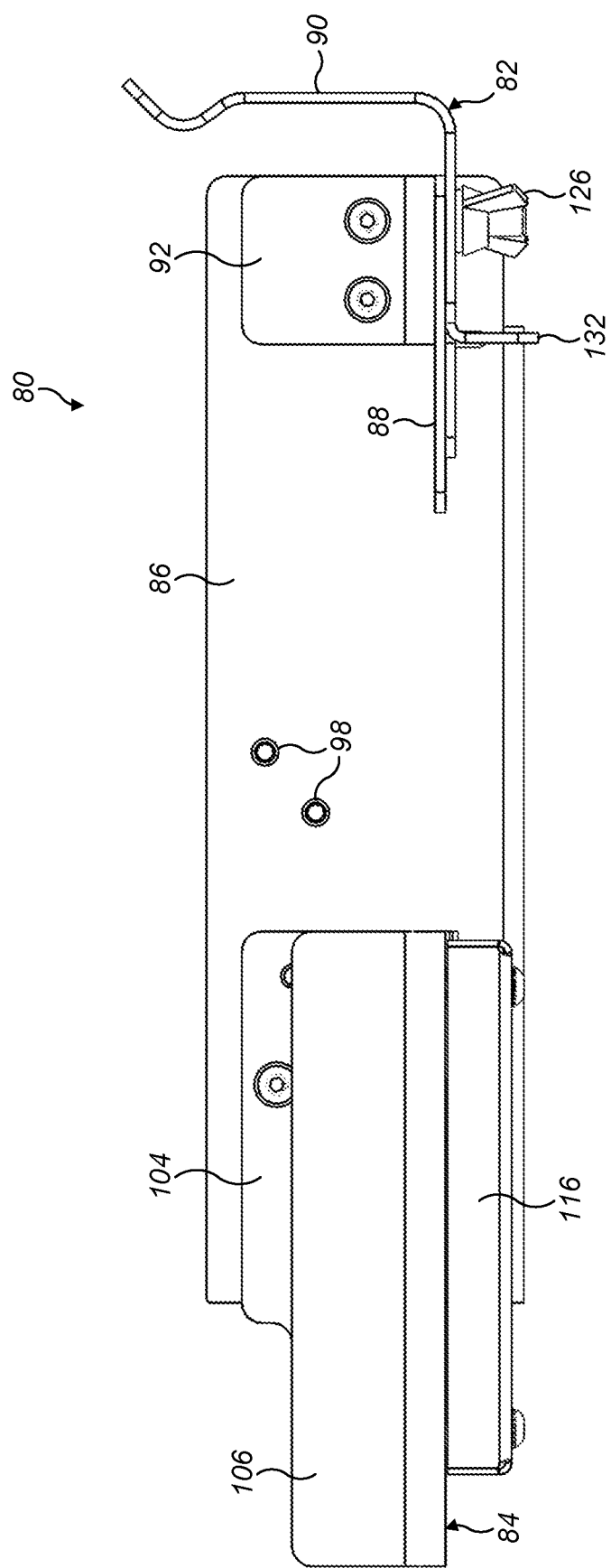
FIG. 11 is a side view the adjustable support of FIG. 9.

In a first configuration, both the first and second support trays 82, 84 are generally flat, aligned and level with each other and spaced apart, as shown in FIGS. 9-11. The first support tray 82 is fitted adjacent to one end of the bracket 86, which is shown to the right in the Figures, and which will usually be towards the rear of the pump in use. The second support tray 84 is fitted towards the other end of the bracket 86, which is shown to the left in the Figures, and which will usually be towards the front of the pump in use. In this first configuration, the equipment holder 80 is able to support a larger bottle, or other item of equipment, in a similar way to that shown in FIG. 3 above.

In a second configuration, the first support tray 82 is attached to a central region of the bracket 86, closer to the second tray 84, as shown in FIGS. 12-15. In addition, the first support tray 82 is secured to the bracket 86 in an angled position. The second support tray 84 is also secured to the bracket 86 in an angled position. In this second configuration, the equipment holder 80 is able to support a smaller bottle, or other item of equipment, such as the type of bottle shown in FIG. 4 above.

The first support tray 82 comprises a base 88, a rear wall 90 and a tab 92 for removable attaching the tray 82 to the bracket 86. The rear wall 90 is preferably movably attached to the base 88 as described further below. The tab 92 preferably defines at least two holes 94 to receive fasteners 96 for attaching the first tray 82 to apertures 98 in the bracket 86. The bracket 86 provides two sets of apertures 98 so that the first support tray 82 can be mounted to the bracket 86 in two different configurations.

In the first configuration, as noted above, the first support tray 82 is fitted adjacent to one end of the bracket 86. The base 88 is substantially horizontal and the rear wall 90 is substantially vertical. The rear wall 90 may include a protrusion 100 for contacting a surface of a bottle supported on the holder 80.

In the second configuration, as noted above, the first support tray 82 is attached to a central region of the bracket 86 in a tilted configuration. Preferably, the base 88 is angled at about 40 degrees to the horizontal and is tilted forwards so that its front edge is lower than its rear edge. Consequently, the rear wall 90 is tilted forwards at about 50 degrees to the horizontal.

Figure 12:
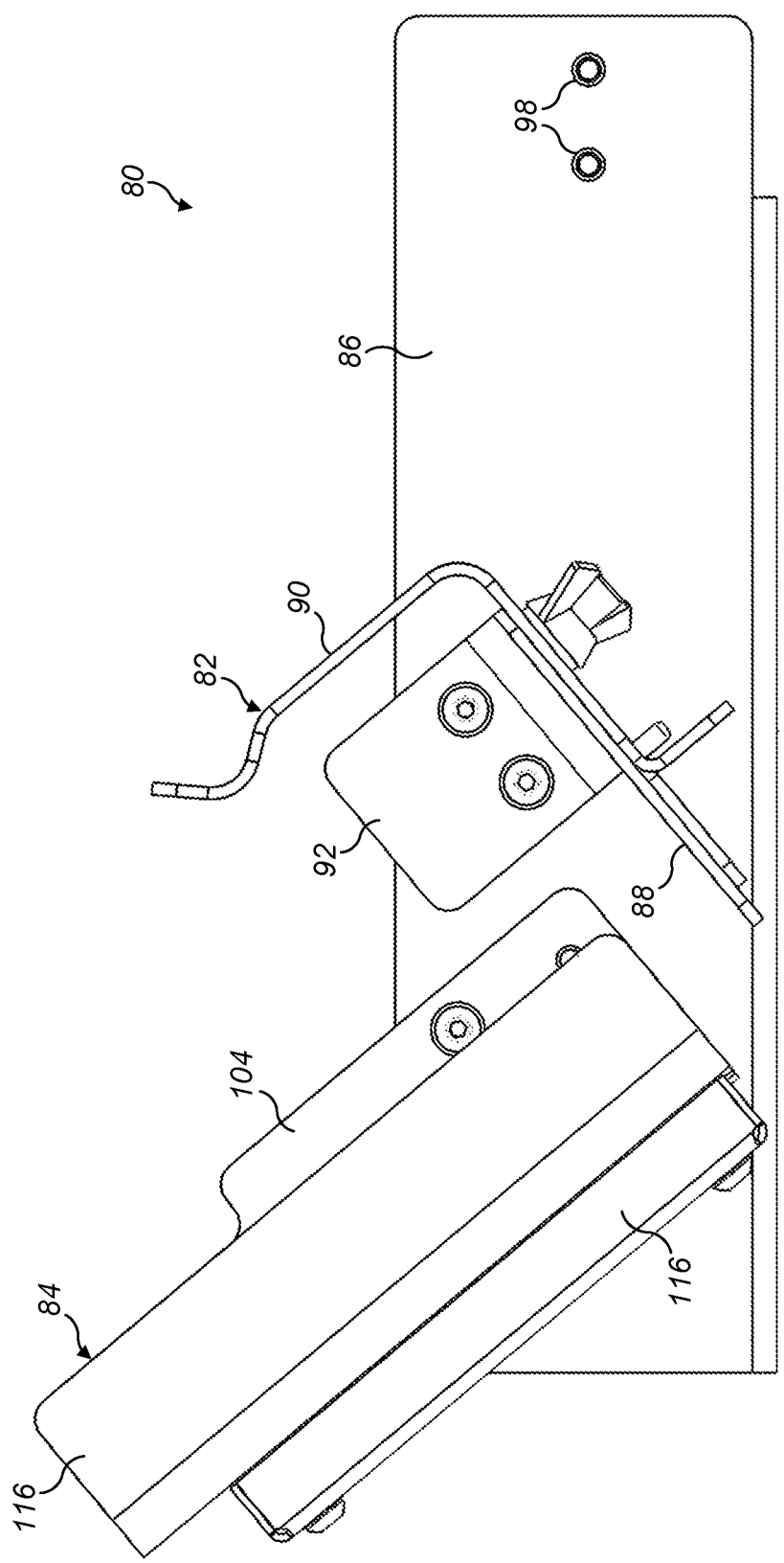
FIG. 12 is a side view of the adjustable support of FIG. 9 in a second, tilted configuration and with the first support tray retracted.

The second tray 84 comprises a base 102 with a first side wall 104 which is attached to the bracket 86 by a pivot 108 allowing the second support tray 84 to rotate between a first flat position in the first configuration, as seen in FIG. 9, and a tilted position in the second configuration, as seen in FIG. 12. Preferably, the second tray 84 further comprises a second side wall 106 on the other side of the base 102, which serves as a retaining wall to prevent dislodgement of a bottle placed on the equipment holder 80.

Any suitable pivot mechanism can be used, including those described above. In this example, the pivot 108 may comprise a pin extending from the first side wall 104 through an opening in the bracket 86. A guide pin 110 may also extend from the first side wall 104 through an arcuate slot 112 in the bracket 86 to guide and limit the extent of rotation of the second support tray 84 about the pivot 108. A stop or catch 114 of any convenient type is also provided to retain the second tray 84 in the second, tilted configuration. This may be a releasable fastener, or a resilient detent as described above. The second support tray could also include a fold-out supporting strut 54 as described above and shown in FIG. 2.

The second tray 84 may optionally include a heating device 116 for heating fluid in a bottle placed on the equipment holder 80, and/or an illumination device 117 to illuminate a bottle to show the liquid level therein, as mentioned above in relation to the first embodiment. The heating device 116 may be secured to the underside of the base 102 of the second tray 84. Where a heating device 116 and/or an illumination device is provided, an additional opening in the bracket 86, such as an additional arcuate slot 118, may be provided for a power cable.

In the first configuration the base 102 of the second tray 84 is substantially horizontal. In the second configuration, the base 102 is tilted with its front edge higher than its rear edge, so the base 102 slopes downwardly towards the rear at approximately 50 degrees to the horizontal.

Preferably, the rear wall 90 of the first tray 82 may also be moved between retracted and extended positions relative to the base 88, to provide further flexibility as to the capacity of the bottle which the equipment holder 80 can accommodate.

Figure 14:
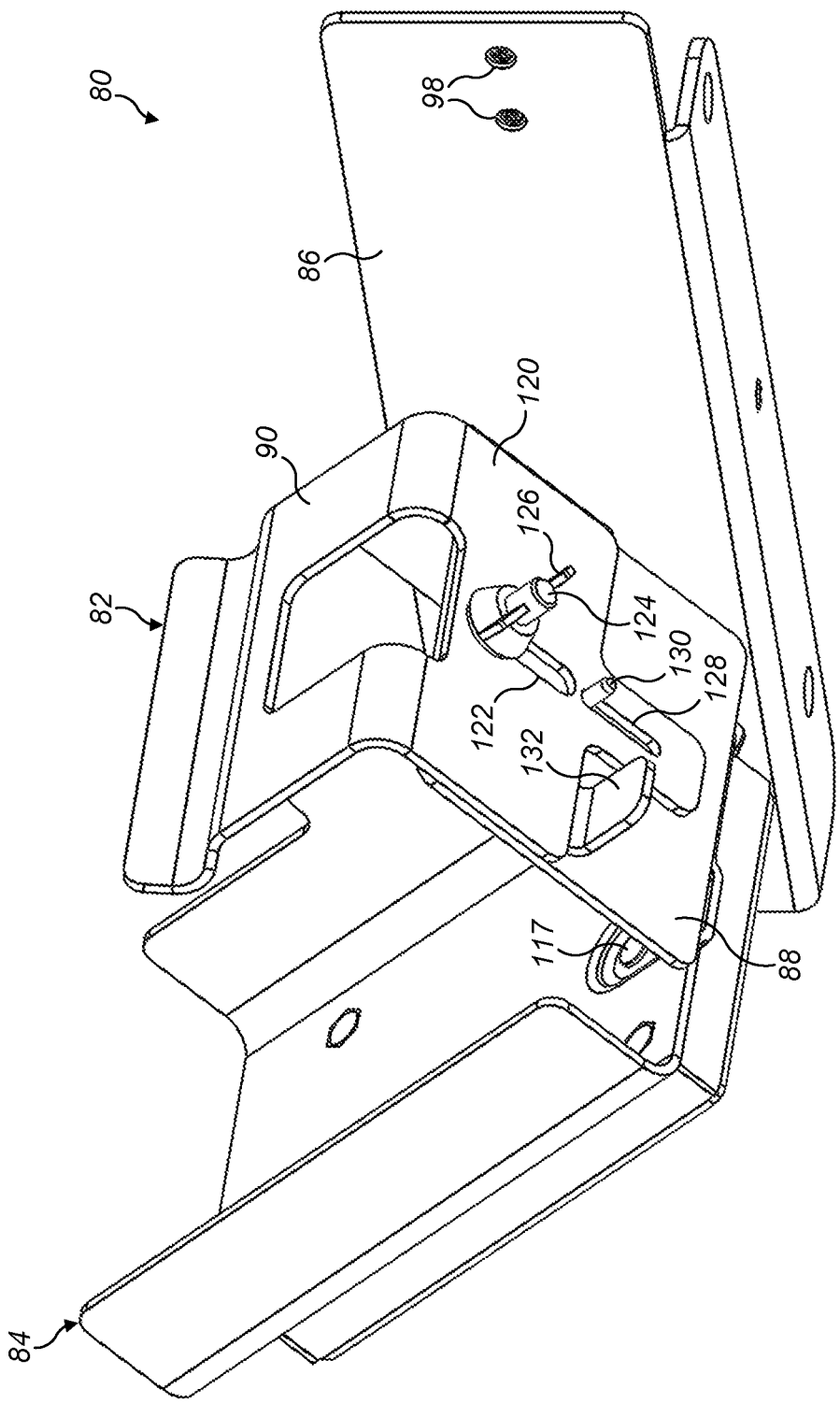
FIG. 14 shows a rear perspective view of the adjustable support of FIG. 12 from the other side and below, and with the first support tray retracted.

As shown in FIG. 14, the rear wall 90 of the first tray 82 may be substantially L-shaped, with a flange 120 joined to or integral with the rear wall 90 and perpendicular thereto. The flange 120 locates immediately beneath the base wall 88. The flange 120 further includes at least one elongate slot 122. A releasable fastener such as bolt 124 protrudes from the underside of the base 88 through the slot 122 and is secured in position, for example by a wingnut 126. Preferably, the flange 120 includes a second elongate slot 128 parallel to the first slot 122 and the base wall 88 includes a guide pin 130 extending from its underside through the second elongate slot 128.

Thus, the rear wall 90 is adjustable relative to the base 88 by loosening the wingnut 126 and sliding the flange 120 relative to the base 88, moving the bolt 124 along the slot 122. The guide pin 130 and second elongate slot 128 help to maintain alignment between the base 88 and the rear wall 90 to prevent relative twisting.

Figure 13:
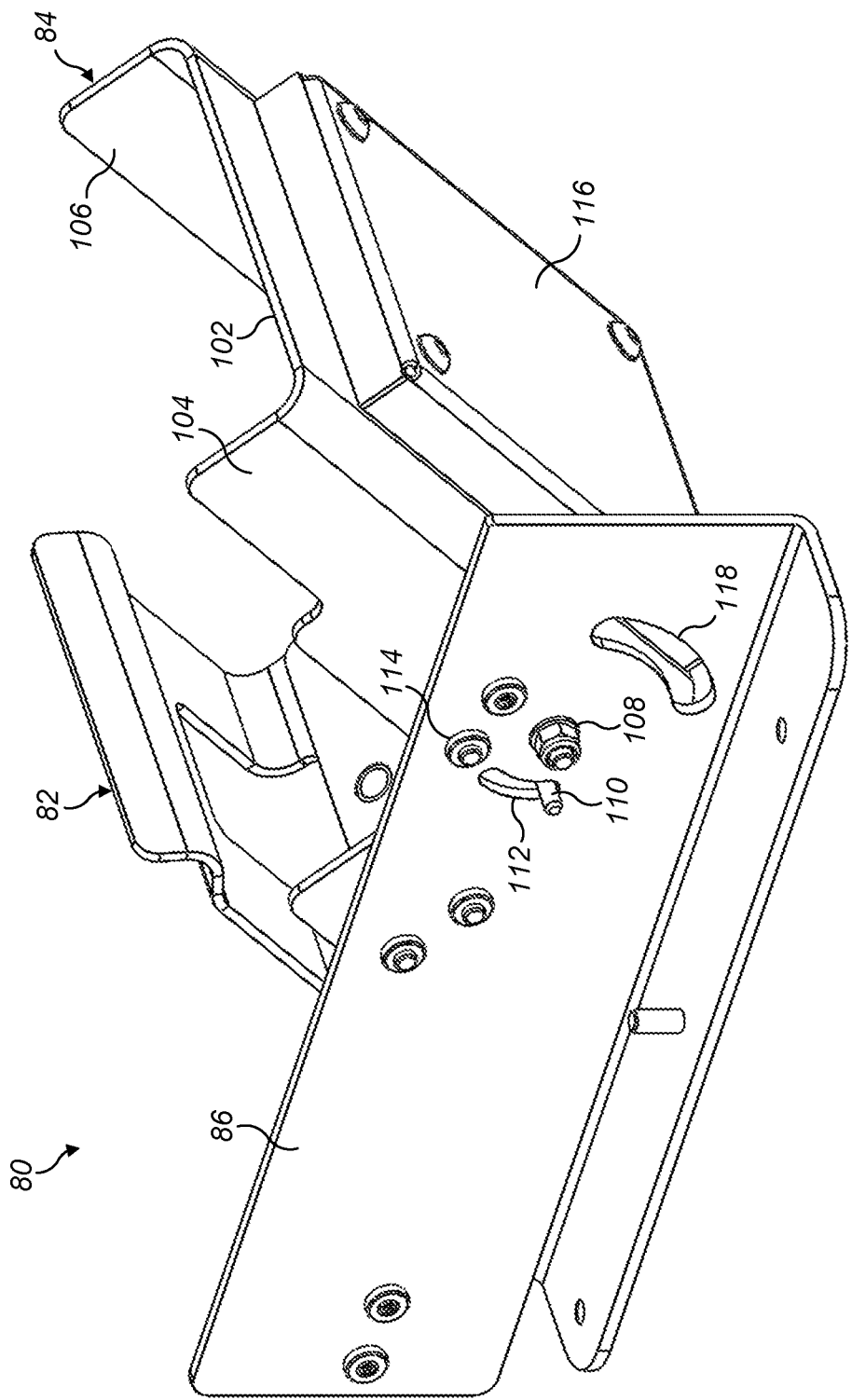
FIG. 13 shows a front perspective view of the adjustable support of FIG. 12 from one side.
Figure 15:
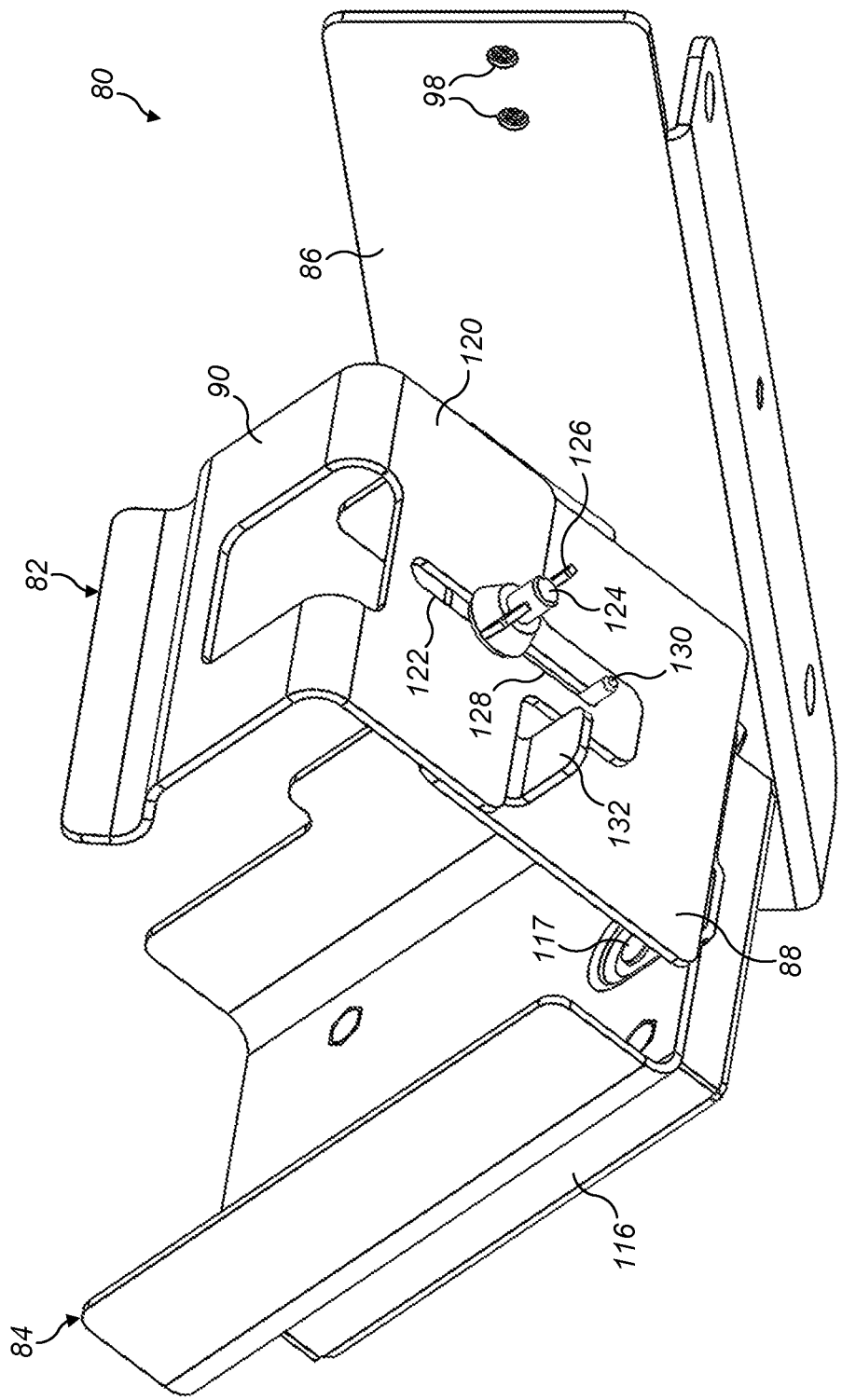
FIG. 15 shows the adjustable support tray of FIG. 14 with the first tray extended.

To accommodate a smaller bottle, the rear wall 90 can be fixed in the retracted position shown in FIGS. 12-14 so that it is close to the rear edge of the base wall 88 and close to the second support tray 84. For a larger bottle, the rear wall 90 can be extended so that it is further from the rear edge of the base 88 and from the second support ray 84, as shown in FIG. 15.

A portion of the flange 120 may also be formed to extend downwardly beneath the first support tray 82 to form a support leg 132. In the first configuration, when the first support tray 82 is horizontal, the support leg 132 extends down vertically and is dimensioned to contact a surface on which a pump 18, to which the holder 80 is attached, is standing. The support leg 132 helps support the weight of an item placed on the equipment holder 80.

Thus the present invention provides an adjustable equipment holder which can be moved between alternative configurations in order to accommodate equipment of various shapes and sizes.

The invention claimed is:

1. An adjustable bottle support for a pump, comprising a first support member and a second support member for supporting parts of a bottle, the first and second support members mounted on an attachment member which is attachable to a pump body, wherein the second support member is pivotally mounted on the attachment member for rotation between a first position in which in which the first and second support members are aligned and level with one another and a second position in which the second support member is tilted and slopes upwardly in a direction away from the first support member, the first support member being horizontal in the first position, the first support member being tilted and sloping upwardly in a direction away from the second support member in the second position, and the first support member being releasably mountable on the attachment member in first and second positions.

2. An adjustable bottle support as claimed in claim 1, wherein the first and second support members each comprise a base with front, rear and side edges, wherein in the first position, the front edge of the first support member and the rear edge of the second support member are level with each other, the second support member is rotatable about a pivot axis between its front and rear edges, and in the second position the rear edge of the second support member is lower than the front edge of the first support member.

3. An adjustable bottle support as claimed in claim 2, wherein the first support member further comprises a downward sloping wall depending from the front edge.

4. An adjustable bottle support as claimed in claim 3, wherein in the second position, the angle between the base of the second support member and the downward sloping wall of the first support member is approximately 90 degrees.

5. An adjustable bottle support as claimed in claim 1, wherein the first support member further comprises a base with a front edge which is closest to the second support member, a rear edge which is furthest from the second support member and a retaining wall which is movably attached to the first support member for movement between a retracted position close to the rear edge and an extended position further from the rear edge.

6. An adjustable bottle support as claimed in claim 1, wherein the second support member is pivotally mounted on the attachment member by a pivot axle and further comprising a detent on the second support member selectively engageable with the attachment member to retain the second support member in the first and second positions.

7. An adjustable bottle support as claimed in claim 6, wherein the detent comprises a resilient arm on the second support member with a projection selectively engageable with first and second openings in the attachment arm.

8. An adjustable bottle support as claimed in claim 7, wherein the resilient arm further comprises a grip portion protruding from the arm and operable by a user to selectively engage and disengage the projection with the first and second openings in the attachment arm.

9. An adjustable bottle support as claimed in claim 1, wherein the second support member further comprises a heating device operable to heat fluid in a bottle supported thereon.

10. An adjustable bottle support as claimed in claim 1, wherein the second support member further comprises an illumination device operable to illuminate a bottle supported thereon.

11. An adjustable bottle support as claimed in claim 1, further comprising a flap attached to the second support member and moveable to a deployed position to hold the second support member in the second position.

12. An adjustable bottle support as claimed in claim 1, wherein the first support member further comprises a downwardly extending support leg.

13. An adjustable bottle support for a pump, comprising a first support member and a second support member for supporting parts of a bottle, the first and second support members mounted on an attachment member which is attachable to a pump body, wherein the second support member is pivotally mounted on the attachment member for rotation between a first position in which in which the first and second support members are aligned and level with one another and a second position in which the second support member is tilted and slopes upwardly in a direction away from the first support member, wherein the second support member is pivotally mounted on the attachment member by a pivot mechanism which comprises three pivot pins extending from the attachment member and arranged in a triangular configuration, the pivot axis of the second support member passes through the centre of the triangular configuration, and the second support member comprises a side wall with three arcuate slots centred on the pivot axis, wherein each pivot pin extends through one of the slots.

14. An adjustable bottle support as claimed in claim 10, wherein the first support member is integral with the attachment member.

15. An adjustable bottle support as claimed in claim 13, wherein each slot comprises first and second ends and a notch is formed at each end for receiving a pivot pin in the first and second positions respectively.

16. An adjustable bottle support as claimed in claim 15, wherein the notches are positioned such that in the first and second positions the weight of the second support member acts to retain each pin in a notch.

17. An adjustable bottle support as claimed in claim 13, wherein the second support member further comprises a heating device operable to heat fluid in a bottle supported thereon.

18. An adjustable bottle support as claimed in claim 13, wherein the second support member further comprises an illumination device operable to illuminate a bottle supported thereon.

19. An adjustable bottle support as claimed in claim 13, further comprising a flap attached to the second support member and moveable to a deployed position to hold the second support member in the second position.

20. An adjustable bottle support as claimed in claim 13, wherein the first support member further comprises a downwardly extending support leg.

* * * * *